US011523737B2

(12) United States Patent
Leizerson et al.

(10) Patent No.: US 11,523,737 B2
(45) Date of Patent: *Dec. 13, 2022

(54) SYSTEM AND METHOD FOR DETERMINING AUDIO CHARACTERISTICS FROM WITHIN A BODY

(71) Applicant: ELBIT SYSTEMS LAND AND C4I LTD, Netanaya (IL)

(72) Inventors: Ilya Leizerson, Netanaya (IL); Barak Alfassi, Netanaya (IL)

(73) Assignee: ELBIT SYSTEMS LAND AND C4I LTD, Netanaya (IL)

( * ) Notice: Subject to any disclaimer, the term of this patent is extended or adjusted under 35 U.S.C. 154(b) by 806 days.

This patent is subject to a terminal disclaimer.

(21) Appl. No.: 16/443,665

(22) Filed: Jun. 17, 2019

(65) Prior Publication Data

US 2019/0365233 A1 Dec. 5, 2019

Related U.S. Application Data

(63) Continuation of application No. 15/578,618, filed as application No. PCT/IL2016/050559 on May 30, 2016, now Pat. No. 10,321,825.

(30) Foreign Application Priority Data

Jun. 1, 2015 (IL) .......................................... 239113

(51) Int. Cl.
*A61B 5/00* (2006.01)
*A61B 7/00* (2006.01)
(Continued)

(52) U.S. Cl.
CPC .......... *A61B 5/0066* (2013.01); *A61B 5/0064* (2013.01); *A61B 5/7207* (2013.01);
(Continued)

(58) Field of Classification Search
CPC ... A61B 5/0066; A61B 5/0064; A61B 5/7207; A61B 5/7435; A61B 7/00; A61B 8/08;
(Continued)

(56) References Cited

U.S. PATENT DOCUMENTS 5,291,885 A * 3/1994 Taniji .................... A61B 3/1233
600/310
5,293,873 A * 3/1994 Fang .................. G01N 29/2418
600/475

(Continued)

FOREIGN PATENT DOCUMENTS

AU 2007100353 A4 12/2007
CN 103730127 A 4/2017
(Continued)

OTHER PUBLICATIONS

Zalevsky, Zeev et al., Simultaneous remote extraction of multiple speech sources and heart beats from secondary speckles pattern, Optics Express, vol. 17, No. 24, pp. 21566-21580, Nov. 23, 2009.
(Continued)

*Primary Examiner* — May A Abouelela
(74) *Attorney, Agent, or Firm* — Knobbe, Martens, Olson & Bear, LLP

(57) ABSTRACT

A system for simultaneously detecting audio-characteristics within a body over multiple body surface locations comprising a coherent light source directing at least one coherent light beam toward the body surface locations, an imager acquiring a plurality of defocused images, each is of reflections of the coherent light beam from the body surface locations. Each image includes at least one speckle pattern, each corresponding to a respective coherent light beam and further associated with a time-tag. A processor, coupled with the imager, determines in-image displacements over time of each of a plurality of regional speckle patterns according to said acquired images. Each one of the regional speckle
(Continued)

patterns is at least a portion of a respective speckle pattern. Each regional speckle pattern is associated with a respective different body surface location. The processor determines the audio-characteristics according to the in-image displacements over time of the regional speckle patterns.

24 Claims, 8 Drawing Sheets

(51) Int. Cl.
- A61B 8/08 (2006.01)
- G02B 27/48 (2006.01)
- G06T 7/246 (2017.01)
- G01H 9/00 (2006.01)
- G01N 21/47 (2006.01)
- G06T 7/20 (2017.01)

(52) U.S. Cl.
CPC ............ A61B 5/7435 (2013.01); A61B 7/00 (2013.01); A61B 8/08 (2013.01); G01H 9/00 (2013.01); G01H 9/002 (2013.01); G01N 21/4788 (2013.01); G02B 27/48 (2013.01); G06T 7/248 (2017.01); A61B 2576/00 (2013.01); G01N 2021/479 (2013.01); G06T 7/20 (2013.01); G06T 2207/30048 (2013.01); G06T 2207/30076 (2013.01)

(58) Field of Classification Search
CPC ...... A61B 2576/00; G01H 9/00; G01H 9/002; G01N 21/4788; G01N 2021/479; G02B 27/48; G06T 7/248; G06T 7/20; G06T 2207/30048; G06T 2207/30076
USPC ......................................................... 600/586
See application file for complete search history.

(56) References Cited

U.S. PATENT DOCUMENTS

| | | | |
|---|---|---|---|
| 7,123,363 B2 * | 10/2006 | Puttappa | A61B 5/1455 356/450 |
| 7,538,859 B2 * | 5/2009 | Tearney | A61B 5/0066 356/35.5 |
| 7,761,139 B2 * | 7/2010 | Tearney | A61B 5/6848 600/476 |
| 7,843,572 B2 * | 11/2010 | Tearney | G01N 21/4795 356/479 |
| 7,859,679 B2 * | 12/2010 | Bouma | G01N 21/4795 356/497 |
| 8,855,749 B2 * | 10/2014 | McKenna | A61B 5/0015 600/475 |
| 8,923,945 B2 * | 12/2014 | McKenna | G06T 11/206 600/323 |
| 9,636,041 B2 * | 5/2017 | Zalevsky | A61B 5/0215 |
| 10,080,091 B2 * | 9/2018 | Iwasaki | G10L 25/18 |
| 10,520,430 B2 * | 12/2019 | Yamazaki | H04N 5/2256 |
| 10,627,519 B2 * | 4/2020 | Iwasaki | H04R 29/00 |
| 2002/0883601 | 12/2002 | Tearney et al. | |
| 2008/0056724 A1 | 3/2008 | Bakish | |
| 2010/0060570 A1 * | 3/2010 | Underkoffler | G06F 3/017 382/103 |
| 2010/0139405 A1 | 6/2010 | Melikechi et al. | |
| 2010/0150404 A1 * | 6/2010 | Marks | A63F 13/211 348/136 |
| 2010/0226543 A1 | 9/2010 | Zalevsky et al. | |
| 2013/0144137 A1 * | 6/2013 | Zalevsky | A61B 5/442 600/314 |
| 2013/0308829 A1 * | 11/2013 | Kawanishi | G06V 20/49 382/118 |
| 2014/0148658 A1 | 5/2014 | Zalevsky et al. | |
| 2016/0066792 A1 * | 3/2016 | Oyama | A61B 5/6823 600/407 |

FOREIGN PATENT DOCUMENTS

| | | |
|---|---|---|
| DE | 10200721 A1 | 7/2003 |
| FR | 2756047 | 5/1998 |
| JP | 2005283160 | 10/2005 |
| WO | 9311553 A1 | 6/1993 |
| WO | 0182786 A2 | 11/2001 |
| WO | 0236015 A1 | 5/2002 |
| WO | 2004037154 A2 | 5/2004 |
| WO | 2004046869 A2 | 6/2004 |
| WO | 2006085252 A2 | 8/2006 |
| WO | 2006085278 A2 | 8/2006 |
| WO | 2008045274 A2 | 4/2008 |
| WO | 2008116010 A1 | 9/2008 |
| WO | 2008120154 A2 | 10/2008 |
| WO | 2008121844 A1 | 10/2008 |
| WO | 2009003903 A1 | 1/2009 |
| WO | 2009008745 A2 | 1/2009 |
| WO | 2009013738 A1 | 1/2009 |
| WO | 2010004365 A1 | 1/2010 |
| WO | 2010096447 A2 | 8/2010 |
| WO | 2011029086 A2 | 3/2011 |
| WO | 2011031428 A2 | 3/2011 |
| WO | 2011032210 A1 | 3/2011 |
| WO | 2011063092 A1 | 5/2011 |
| WO | 2012096878 A2 | 7/2012 |
| WO | 2012100048 A1 | 7/2012 |
| WO | 2012101644 A2 | 8/2012 |
| WO | 2012112977 A1 | 8/2012 |
| WO | 2012143798 A1 | 10/2012 |
| WO | 2013049123 A1 | 4/2013 |
| WO | 2013160861 A1 | 10/2013 |
| WO | 2013188520 A2 | 12/2013 |
| WO | 2014020611 A1 | 2/2014 |
| WO | 2014043166 A1 | 3/2014 |
| WO | 2014116483 A1 | 7/2014 |
| WO | 2014151114 A1 | 9/2014 |
| WO | 2014164363 A1 | 10/2014 |
| WO | 2014175154 A1 | 10/2014 |

OTHER PUBLICATIONS

International Search Report dated Sep. 13, 2016 for International Application No. PCT/IL2016/050559, 5 pages.
Written Opinion of the International Searching Authority dated Sep. 13, 2016 for International Application No. PCT/IL2016/050559, 6 pages.
Extended European Search Report dated Jul. 6, 2015, for EP Application No. 16802686.2 in 8 pages.
Chen, et al., Audio signal reconstruction based on adaptively selected seed points from laser speckle images, Optics Communications, vol. 331, pp. 6-13, May 28, 2014.
Beiderman, et al., Automatic solution for detection, identification and biomedical monitoring of a cow using remote sensing for optimised treatment of cattle, Journal of Agricultural Engineering 2014; vol. XLV:418, pp. 153-160, Oct. 6, 2014.
Diazdelacruz, Jose M., Adaptive aperature defocused digital speckle photography, Department of Applied Physics, Faculty for Industrial Engineering, Polytechnic University of Madrid, pp. 1-14, Feb. 2, 2008.
Donati, Silvano, Self-mixing interferometry for biomedical signals sensing, IEEE Journal of Selected Topics in Quantum Electronics, vol. 20, No. 2, Mar./Apr. 2014.
Gaudette, et al., Speckle metrology to heart mechanics, State University of New York at Stony Brook, Division of Cardiothoracic Surgery, Department of Mechanical Engineering, Stony Brook, NY, pp. 353-363.
Greated, et al., Sound Measurement Using Speckle Interferometry, Forum Acusticum, Budapest, 2005.
Jokela, et al., Deep Breeze Brings an Innovative Medical Device to Market, INSEAD, The Business School for the World, Israel Research Centre, HMI/Social Innovation Centre, Nov. 2009.
Periasamy, et al., Detection of human cardiac activity at apex region by laser speckle, Current Science, Biomedical Engineering Division, Indian Institute of Technology, India, vol. 50, No. 7, pp. 302-304, Apr. 5, 1981.

(56) References Cited

OTHER PUBLICATIONS

Mor, et al., Breath sound distribution images of patients with pneumonia and pleural effusion, Respiratory Care, vol. 52, No. 12, pp. 1753-1760, Dec. 2007.

Ramachandran, et al., Three-dimensional reconstruction of cardiac displacement patterns on the chest wall during the P, QRS and T-segments of the ECG by laser speckle interferometry, Biomedical Engineering Divsion Indian Institute of Technology Madras India, IFMBE, Oct. 12, 1988.

Scalise, Lorenzo, Non Contact Heart Monitoring, Advances in Electrocardiograms—Methods and Analysis, Jan. 2012, http://www.intechopen.com/books/advances-in-electrocardiograms-methods-and-analysis/non-contact-heartmonitoring.

Sun, Shih-Yu, Single-pixel laser microphone, Massachusetts Institute of Technology.

Sabatier, et al., Vibration sensors for buried landmine detection, The Journal of the Acoustical Society of America, 39(113): 1146-11541333, Jan. 2001.

\* cited by examiner

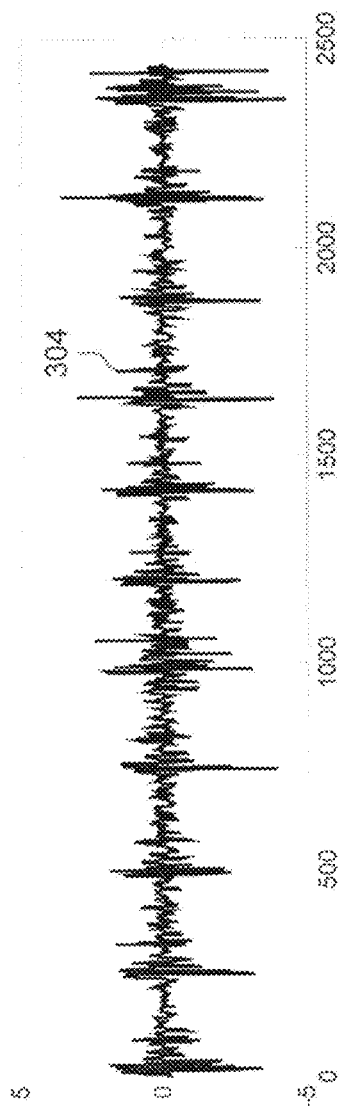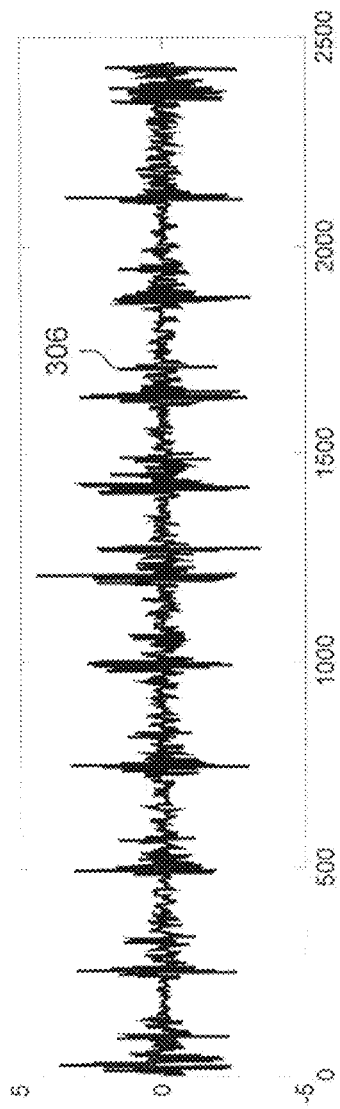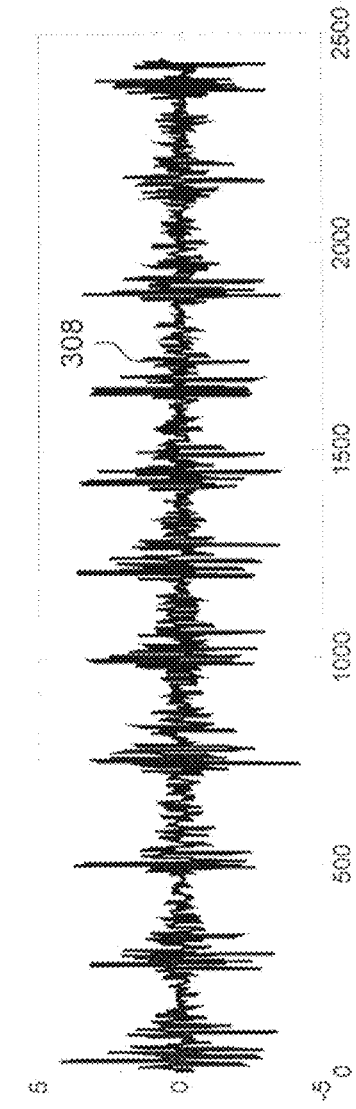

SYSTEM AND METHOD FOR DETERMINING AUDIO CHARACTERISTICS FROM WITHIN A BODY

INCORPORATION BY REFERENCE TO ANY PRIORITY APPLICATIONS

This application is a continuation of U.S. patent application Ser. No. 15/578,618, filed Nov. 30, 2017, which is the U.S. National Phase Application under 35 U.S.C. § 371 of International Application No. PCT/IL2016/050559, filed May 30, 2016, designating the U.S. and published as WO 2016/193970 A1 on Dec. 8, 2016 which claims the benefit of Israel Patent Application No. 239113, filed Jun. 1, 2015, all of which are hereby incorporated by reference in their entireties.

FIELD OF THE DISCLOSED TECHNIQUE

The disclosed technique relates to speckle metrology in general, and to systems and methods for simultaneously determining audio characteristics from within a body over multiple body surface locations, in particular.

BACKGROUND OF THE DISCLOSED TECHNIQUE

Detecting sound by employing laser speckle interferometry is known in the art. To that end a laser beam is projected toward the sound source or on to a surface acoustically coupled with the sound source (i.e., a surface which vibrates according to the sound produced by the sound source). The laser beam impinges on the surface and diffusively reflects therefrom. The diffusive reflection of different portions of the light beam results in a random shift of the phases of the portions of the corresponding light waves and a random distribution of the intensities thereof. Consequently, the waves corresponding to the diffusively reflected portions of the beam interfere with each other. This results in a light distribution with varying intensity. These random variations in the intensity create a speckle pattern for each light beam. The speckle pattern varies with the vibrations of the surface. An imager acquires an image of the reflection of the laser beam from the surface. These images of the reflection of the laser beam include speckle patterns. The shift of the speckle patterns between subsequent images is related to the vibrations of the surface and thus to the sound produced by the sound source.

Reference is now made to FIG. 1, which is a schematic illustration of a system, generally referenced 10, for determining the vibrations of an object, which is known in the art. System 10 includes an imager 12. Imager 12 includes an imaging sensor 14 and a lens 16. Lens 16 is optically coupled with imaging sensor 14. A beam of coherent light 18 (e.g., a laser light) impinges on the surface of an object 20 and diffusively reflects therefrom. As mentioned above, this diffusive reflection results in a speckle pattern. Imager 12 acquires the speckle patterns in a defocused image plane 22. This defocused image plane is located at a distance Z from the object. The angular displacement of the object results in a shift, $\Delta H$, of the speckle pattern in defocused image plane 22 and thus of the speckle pattern in the acquired image.

The publication to Zalevsky et al. entitled "Simultaneous Remote Extraction of Multiple Speech Sources and Heart Beats from Secondary Speckles Pattern" directs to a system for extraction of remote sounds. In the system directed to by Zalevsky, a laser beam is directed toward an object and employs a defocused image and detects temporal intensity fluctuations of the imaged speckles pattern and their trajectory. From the trajectories of the speckles pattern the system directed to by Zalevsky detects speech sounds and heartbeat sounds.

U.S. Pat. No. 8,286,493 to Bakish, entitled "Sound Source Separation and Monitoring Using Direction Coherent Electromagnetic Waves" directs to a system and methods in which a plurality of laser beams are pointed toward multiple sound sources. The reflection of each of the beams is related to a corresponding sound source. The speckle pattern resulting from the reflection of each beam is analyzed to determine the sound produced by the corresponding source. Thus, source separation may be achieved.

The publication to Chen et al., entitled "Audio Signal Reconstructions Based on Adaptively Selected Seed Points from Laser Speckle Images" directs to a method for estimating the vibrations of an object according to variations in the gray level values of selected pixels, also referred to as seed points, in a defocused image of the speckle pattern. To that end, the method directed to Chen acquires a plurality of images and determines a linear correspondence between the variations in the gray level values of the seed points and the vibration of the object by estimating the parameters that minimize the difference between the vibration of the object at two different seed points, across all images (i.e., since the difference between the equations are used the vibration is not a parameter in the optimization). The vibration between images is determined as the weighted sum of the vibration due to each seed point.

The publication entitled "Breath Sound Distribution of Patient With Pneumonia and Pleural Effusion" to Mor et al., describes the experimental results of a system for detecting a breath sound distribution map. The system directed to by Mor includes 40 contact sound sensors, assembled on two planar arrays, which cover the posterior lung area. The sensors are attached to the patient's back by low-suction vacuum controlled by a computer. The sounds captured by the sensors are filtered to the desired frequency range of breath (between 150-250 Hertz). The signals are processed and the breath sound distribution is displayed as a grayscale image. Areas with high lung vibration energy appear black and areas with low lung vibration energy appear light grey. A physician identifies whether the patient is suffering from Pneumonia or Pleural Effusion based on these images.

PCT Application Publication 2002/036015 to Tearney et al directs to employing focused images of laser speckles for measuring microscopic motion (e.g., resulting from blood flow), such as Brownian motion of tissue in vivo, to gather information about the tissue. According to D1, coherent or partially coherent light is reflected from the tissue to form a speckle pattern at a detector. Due to motion of reflectors within the tissue, the speckle pattern changes over time. In operation, coherent light, such as laser light is transmitted through optical fiber toward a tissue sample (e.g., static tissue, moving tissue, atherosclerotic plaque and the like). The device can be placed directly in contact with the sample or a short distance therefrom. The light enters the sample, where it is reflected by molecules, cellular debris or microstructures (such as organelles, microtubules), proteins, cholesterol crystals. The light remitted from the sample is focused on the distal end of a fibers array (fibroscope). The focused light travels through the fibers to a CCD detector. Due to interference, a speckle pattern forms at the CCD detector. The resulting speckle image is analyzed. According to Tearney, a reference image is acquired and correlated with successive images. Since the speckle pattern is each successive image is different the correlation between the acquired image and the reference image decreases. According to Tearney, various physiological conditions can be determined from the de-correlation time constant. It is noted that Tearney does not measure the motion that cause the change in the speckle pattern just the result of such a motion. Furthermore, Tearney directs to illuminating multiple locations of the tissue in succession, forming a separate series of speckle patterns for each respective location, and then analyzing each separate series of speckle patterns and comparing the separate series to deduce structural and/or biomechanical differences between the respective locations of the tissue.

SUMMARY OF THE PRESENT DISCLOSED TECHNIQUE

It is an object of the disclosed technique to provide a novel method and system for simultaneously detecting audio characteristics from within a body, over multiple body surface locations.

In accordance with the disclosed technique, there is thus provided a system for simultaneously detecting audio characteristics from within a body, over multiple body surface locations. The system includes a coherent light source, an imager and a processor. The processor is coupled with the imager. The coherent light source directs at least one coherent light beam toward the body surface locations. The at least one coherent light beam impinges on the body surface locations. The imager acquires a plurality of defocused images, each image is of reflections of the at least one coherent light beam from the body surface locations. Each image includes at least one speckle pattern, each speckle pattern corresponds to a respective one of the at least one coherent light beam. Each image is further associated with a time-tag. The processor determines in-image displacements over time of each of a plurality of regional speckle patterns according to the acquired images. Each one of the regional speckle patterns is at least a portion of a respective one of the at least one speckle pattern. Each one of the regional speckle patterns is associated with a respective different one of the body surface locations. The processor determines the audio characteristics according to the in-image displacements over time of the regional speckle patterns.

In accordance with another aspect of the disclosed technique, there is thus provided method for simultaneously detecting audio characteristics within a body, over multiple body surface locations. The method includes the procedures of directing at least one coherent light beam toward the body surface locations, acquiring a plurality of defocused images of the body surface locations, determining the in-image displacement over time in each of a plurality of regional speckle patterns according to the acquired images and determining the audio characteristics originating from within the body at each of the body surface locations according to the in-image displacement over time in the respective regional speckle pattern. The at least one coherent light beam impinges on the body surface locations. Each image is of reflections of the at least one coherent light beam from the body surface locations. Each image includes at least one speckle pattern, each corresponds to a respective one of the at least one coherent light beam. Each image is associated with a time-tag. Each one of the regional speckle patterns is at least a portion of a respective one of the at least one speckle pattern. Each one of the regional speckle patterns is associated with a respective different one of the body surface locations.

BRIEF DESCRIPTION OF THE DRAWINGS

The disclosed technique will be understood and appreciated more fully from the following detailed description taken in conjunction with the drawings in which:

FIGS. 6A-6D are schematic illustrations of an example for simultaneously detecting audio characteristics within a body, over multiple body surface locations, in accordance with another embodiment of the disclosed.

DETAILED DESCRIPTION OF THE EMBODIMENTS

The disclosed technique overcomes the disadvantages of the prior art by providing a system and a method for simultaneous detection of audio characteristics within a body, over multiple body surface locations. The term "audio characteristics" relate herein to an audio signal of a sound produced from within the body or to the characteristics of that sound (e.g., spectrum, spectrogram, sound pressure level, sound power, time delay between signals measured on different body surface locations, energy and the like). The sound from within the body may be produced, for example, by an organ (e.g., the heart, the lungs, the stomach or the intestines). The sound from within the body may also be that produced by an embryo (e.g., by the heart of the embryo or by the motion of the embryo within the womb). The system according to the disclosed technique includes a coherent light source, which directs at least one coherent light beam toward body surface locations and an imager, which acquires a plurality of defocused images of the reflections of the at least one coherent light beam from the body surface locations. Each image includes at least one speckle pattern corresponding to a respective coherent light beam. Each image is further associated with a time-tag. A processor, coupled with the imager, determines in-image displacement over time of each of a plurality of regional speckle patterns according to the acquired images. Each one of the regional speckle patterns being at least a portion of a respective speckle pattern associated therewith (e.g., two regional speckle patterns may be a portion of a single speckle pattern). Each of the regional speckle patterns is associated with a respective different one of the body surface locations. In other words, each of at least a portion of a speckle pattern may be associated with a different body surface location and define a regional speckle pattern. The processor determines the audio characteristics originating from within the body at each of the body surface location, according to the in-image displacement over time of the respective regional speckle pattern. The processor compares the determined audio characteristics with stored audio characteristics corresponding to known physiological conditions, thereby attempting to detect at least one physiological condition. A graphical representation of these audio characteristics may be displayed on a display. A motion compensator compensates for the effects of relative motion between the patient and the imager, on the determined audio characteristics. An audio reproduction sub-system may reproduce the sounds from within the body according to the determined sound signal. Also, a user may select the locations of interest corresponding to the regional speckle patterns with the aid of a user interface (UI).

Figure 1:
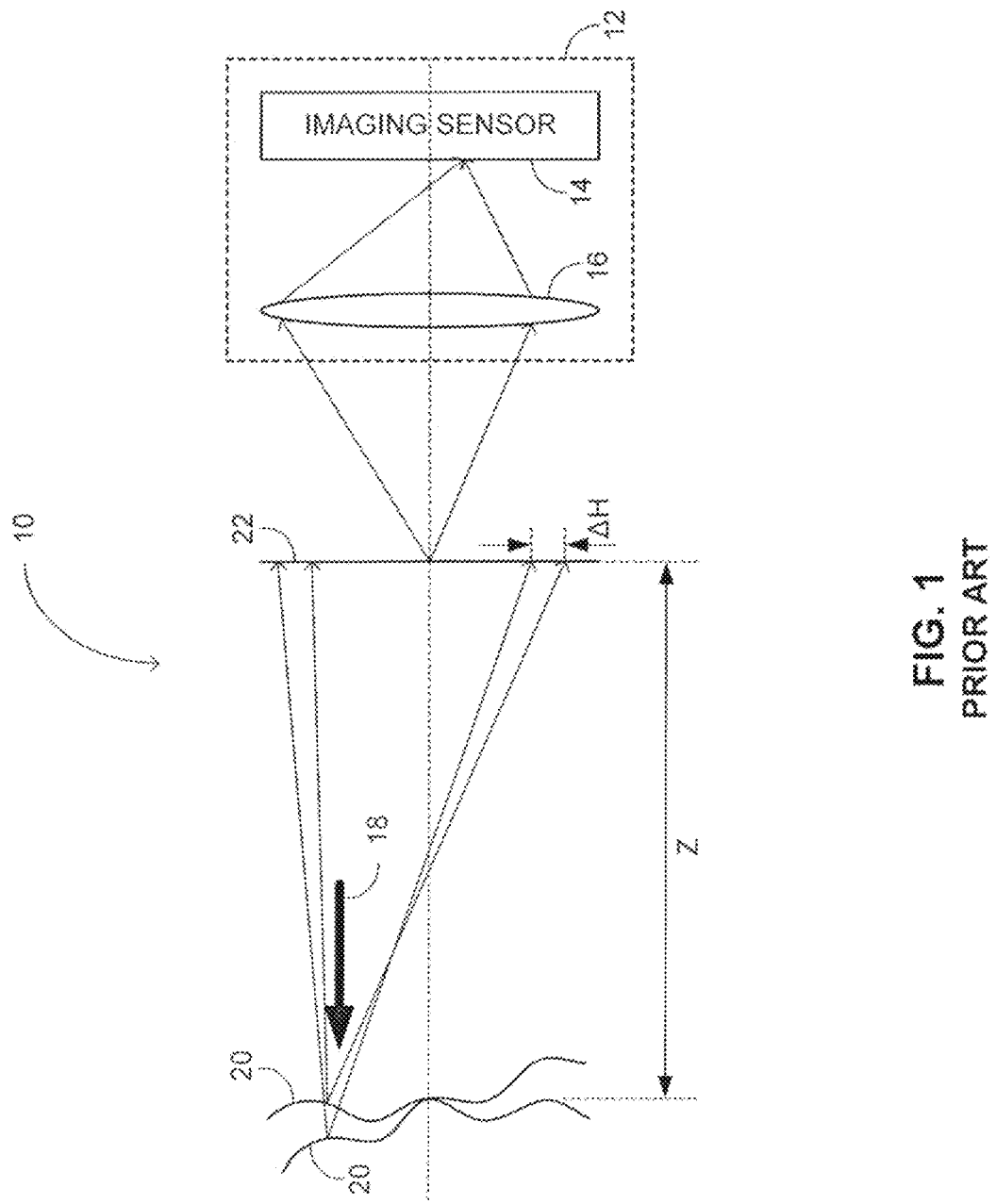
FIG. 1 is a schematic illustration of a system for determining the vibrations of an object, which is known in the art.
Figure 2:
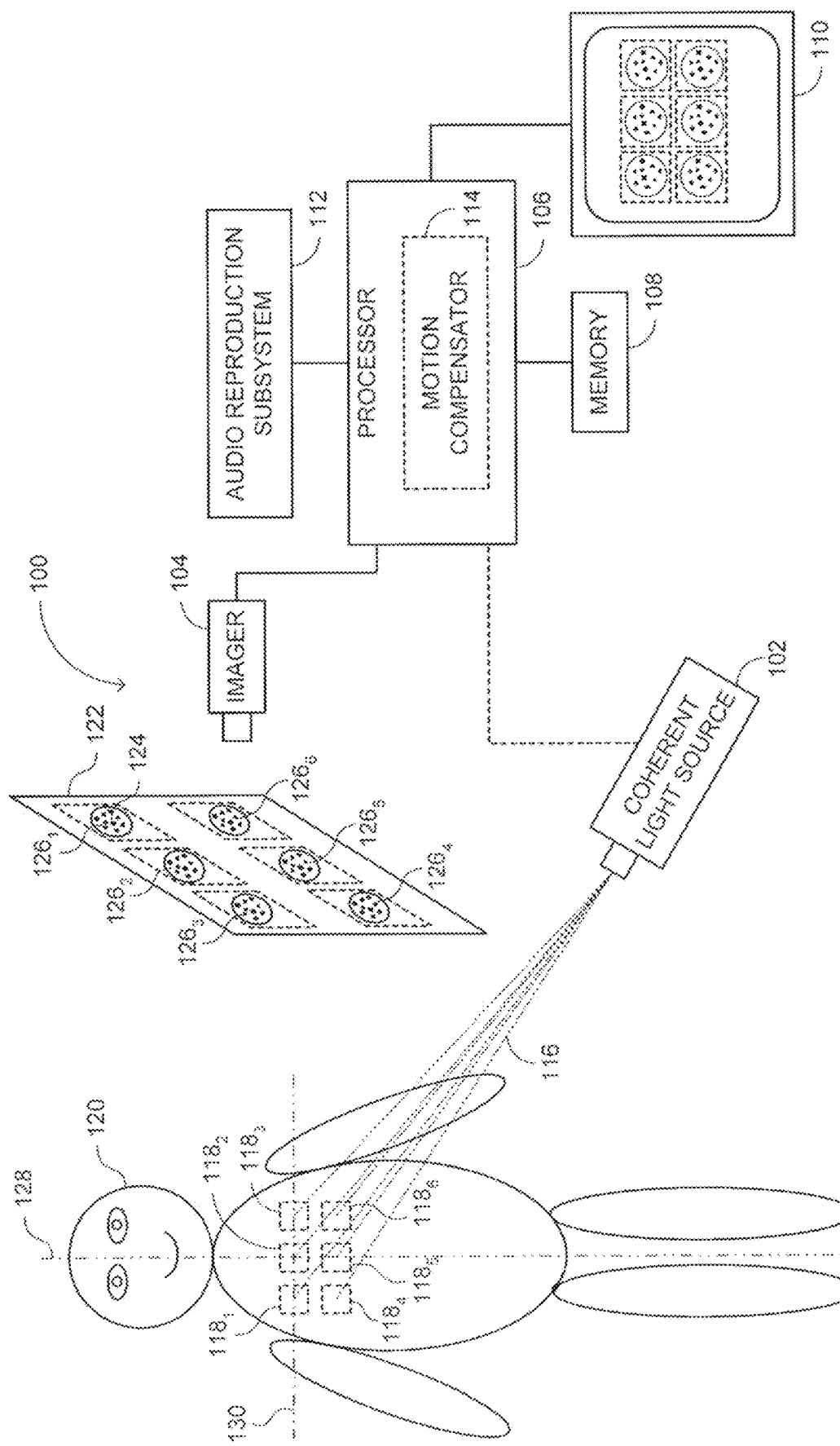
FIG. 2 is a schematic illustration of a system for simultaneously detecting audio characteristics within a body, over multiple body surface locations, constructed and operative in accordance with an embodiment of the disclosed technique.

Reference is now made to FIG. 2, which is a schematic illustration of a system, generally referenced 100, for simultaneously detecting audio characteristics within a body, over multiple body surface locations, constructed and operative in accordance with an embodiment of the disclosed technique. System 100 includes a coherent light source 102, an imager 104, a processor 106, a memory 108, a display 110 and an audio reproduction sub-system 112. Processor 106 includes a motion compensator 114. Processor 106 is coupled with imager 104, memory 108, display 110 and with audio reproduction sub-system 112. Processor 106 is optionally coupled with coherent light source 102 (i.e., as indicated by the hatched line in FIG. 1).

Coherent light source 102 emits a beam or beams of monochromatic coherent light. Coherent light source 102 is, for example, a laser light source. Imager 104 includes an imager sensor array (not shown) such as a Charged Coupled Device (CCD) sensor array or Complementary Metal Oxide Semiconductor (CMOS) sensor array sensitive at the wavelength of the light emitted by coherent light source 102.

Coherent light source 102 emits a plurality of light beams, such as light beam 116, each toward a respective one of a plurality of body surface locations $118_1$, $118_2$, $118_3$, $118_4$, $118_5$ and $118_6$ of patient 120. Each of the plurality of light beams impinges on the respective one of body surface locations $118_1$, $118_2$, $118_3$, $118_4$, $118_5$ and $118_6$, and diffusively reflects therefrom (i.e., each ray is reflected at a random direction) which, as mentioned above, results in a speckle pattern across each light beam.

Imager 104 acquires a plurality of defocused images, such as image 122, of reflections of the light beams from body surface locations $118_1$-$118_6$. Each image including a plurality of speckle patterns such as speckle pattern 124. Each one of the speckle patterns corresponds to a respective light beam reflected from body surface locations $118_1$-$118_6$. Thus, each of the speckle patterns correspond to a respective body surface location $118_1$-$118_6$. Imager 104 further associates each image with a respective time-tag. Imager 104 provides the images acquired thereby to processor 106.

Processor 106 determines the in-image displacement over time in each of a plurality of regional speckle patterns $126_1$, $126_2$, $126_3$, $126_4$, $126_5$ and $126_6$ according to the acquired images. Each one of the regional speckle patterns $126_1$-$126_6$ is associated with a respective different one of the body surface locations $118_1$-$118_6$. In the example set forth in FIG. 2, each regional speckle patterns $126_1$-$126_6$ is also associated with a different respective speckle pattern (i.e., no two regional speckle patterns are associated with the same respective speckle patter). In the defocused images, the vibrations and motion of the body surface locations $118_1$-$118_6$ result in an in-image displacement of the corresponding regional speckle patterns $126_1$, $126_2$, $126_3$, $126_4$, $126_5$ and $126_6$ between two images. The term 'in-image displacement' herein relates to the difference between the pixel coordinates of the speckle pattern (e.g., of the center of mass of the speckle pattern) in two different images. Processor 106 may determine the in-image displacements over time in each of a plurality of regional speckle patterns $126_1$-$126_6$. As further explained below, processor 106 determines the vibrations of each one of body surface locations $118_1$-$118_6$. These vibrations may be caused by sound produced from within the body. Thus, processor 106 determines the audio characteristics at body surface locations $118_1$-$118_6$, according to in-image displacements over time in the respective regional speckle patterns $126_1$-$126_6$. As mentioned above, the vibrations of body surface locations $118_1$-$118_6$, and thus the audio characteristics corresponding thereto, may be induced from within body. It is also noted that at least some of body surface locations $118_1$-$118_6$ may partially overlap with each other thereby increasing the spatial resolution of the system.

Following is an example of determining the vibrations of each one of body surface locations $118_1$-$118_6$, and thus of the audio characteristics thereof, according to the plurality of images of the respective regional speckle patterns $126_1$-$126_6$. Processor 106 cross-correlates each pair of successive selected ones of the acquired images (i.e., as determined according to the time-tag associated with each image). Processor 106 determines the relative shift between each successive pair of images accordingly to the result of the respective cross-correlations (e.g., according to the location of the maxima of the result of the cross-correlation). Processor 106 determines the vibration of body surface locations $118_1$-$118_6$ according to the relative shift between each successive pair of images. The angular displacement of the body about a vertical axis 128 results in a corresponding horizontal shift of the regional speckle patterns $126_1$, $126_2$, $126_3$, $126_4$, $126_5$ and $126_6$ in the defocused image plane. The angular displacement of the body about a horizontal axis 130 results in a vertical shift of the regional speckle pattern $126_1$, $126_2$, $126_3$, $126_4$, $126_5$ and $126_6$ in the defocused image plane. Thus, the angular displacement of the body about the vertical axis 128 or horizontal axis 130 results in a corresponding shift of the regional speckle patterns $126_1$, $126_2$, $126_3$, $126_4$, $126_5$ and $126_6$ in the acquired image as well. The relationship between the angular displacement of the body surface location about a single axis and the corresponding shift of a speckle pattern in a successive pair of acquired images is as follows:

$$\theta = \frac{2ZM}{\Delta h} \quad (1)$$

where $\theta$ is the angular displacement (i.e., either about the vertical axis or the horizontal axis) of the body surface location, Z is the distance between the body surface location and the defocused image plane, M is the magnification of the optics of imager 104 and $\Delta h$ is the corresponding relative shift (i.e., either horizontal or vertical) between the speckle patterns in a pair of successive images (i.e., as determined by the cross-correlation between the images). Alternatively, Processor 106 determines the vibrations of each one of body surface locations $118_1$-$118_6$, and thus of—the audio characteristics thereof, according to variation of selected seed points as described above.

During the acquisition of the images, either patient 120 or imager 104 or both, may move. This relative motion between patient 120 and imager 104, also referred to herein as 'common motion', results in an additional shift in the regional speckle patterns (i.e., other than the shift caused by the vibration of body surface locations $118_1$-$118_6$). Thus, the total shift of one of regional speckle patterns $126_1$, $126_2$, $126_3$, $126_4$, $126_5$ and $126_6$ (i.e., both due to the vibration of the body surface locations $118_1$-$118_6$ and due to the common motion), in a single image axis (i.e., either the x axis or the y axis of the image) and between two subsequent images is as follows:

$$\begin{pmatrix} ds_1(t) \\ ds_2(t) \\ \vdots \\ ds_N(t) \end{pmatrix} + \begin{pmatrix} a_{1,1} & a_{1,2} & a_{1,3} & a_{1,4} & a_{1,5} & a_{1,6} \\ a_{2,1} & a_{2,2} & a_{2,3} & a_{2,4} & a_{2,5} & a_{2,6} \\ \vdots & \vdots & \vdots & \vdots & \vdots & \vdots \\ a_{N,1} & a_{N,2} & a_{N,3} & a_{N,4} & a_{N,5} & a_{N,6} \end{pmatrix} \cdot \begin{pmatrix} dx(t) \\ dy(t) \\ dz(t) \\ dYaw(t) \\ dPitch(t) \\ dRoll(t) \end{pmatrix} = \begin{pmatrix} dS_1(t) \\ dS_2(t) \\ \vdots \\ dS_N(t) \end{pmatrix} \quad (2)$$

In Equation (2), N relates to the number of regional speckle patterns, $ds_i(t)$ relates to the in-image displacement (i.e., occurring between the acquisition of two subsequent images) of a regional speckle pattern corresponding to body surface location i only due to the vibration thereof. $dSi(t)$ relates to the in-image displacement (i.e., also occurring between the acquisition of two subsequent images) of the regional speckle pattern corresponding to body surface location i due to both the vibration thereof and the common motion. Further in equation (2) $a_{i,j}$ are common motion coefficients in a motion compensation matrix. A respective motion compensation matrix is associated with each regional speckle pattern. Also in Equation (2) $dx(t)$, $dy_i(t)$, $dz_i(t)$ relate to the change in the relative position between patient 120 and imager 104 (i.e., between the acquisition times of the two subsequent images) in the x, y and z axes respectively and $dYaw_i(t)$, $dPitch_i(t)$ and $dRoll_i(t)$ relate to the change in the relative orientation between patient 120 and imager 104 (i.e., also between the acquisition times of two subsequent images) about the yaw, pitch and roll axes respectively. In vector and matrix notation, equation 2 may be expressed as follows:

$$\vec{s}(t) + M\vec{F}(t) = \vec{S}(t) \quad (3)$$

M is referred to herein as the 'motion compensation matrix' where the entries thereof are $a_{i,j}$ of equation (2), $\vec{s}(t)$ is a vector where the entries thereof are $ds_i(t)$ of equation (2), $\vec{S}(t)$ is a vector where the entries thereof are $dS_i(t)$ of equation (2) and $\vec{F}(t)$, referred to herein as the 'relative motion vector' is a vector where the entries thereof are $dx(t)$, $dy_i(t)$, $dz_i(t)$, $dYaw_i(t)$, $dPitch_i(t)$ and $dRoll_i(t)$. According to equation (3), the displacement of the regional speckle pattern corresponding to body surface locations $118_1$-$118_6$, only due to the vibration of the body surface locations, may be expressed as follows:

$$\vec{s}(t) = \vec{S}(t) - M\vec{F}(t) \quad (4)$$

To compensate for relative motion between patient 120 and imager 104, motion compensator 114 requires information relating to $\vec{S}(t)$, $\vec{F}(t)$ and M. $\vec{S}(t)$ is determined from the acquired images by employing a cross-correlation between a pair of successive images, as mentioned above. M is determined either during a calibration process or analytically as further explained below. Thus, only $\vec{F}(t)$ is unknown.

Assuming that the average in-image displacement of regional speckle pattern $126_1$, $126_2$, $126_3$, $126_4$, $126_5$ and $126_6$ corresponding to body surface locations $118_1$-$118_6$, only due to the vibration thereof, is small relative to the in-image displacement due to the common motion, the in-image displacement due to the relative motion between patient 102 and imager 104 may be estimated as follows:

$$M\vec{F}(t) = \vec{S}(t) \quad (5)$$

Motion compensator 114 may estimate $\vec{F}(t)$ by employing the least squares method as follows:

$$\vec{F}(t) = [M^T M]^{-1} M^T \vec{S}(t) \quad (7)$$

Thus, processor 106 determines the shift of regional speckle patterns $126_1$, $126_2$, $126_3$, $126_4$, $126_5$ and $126_6$ corresponding to body surface locations $118_1$-$118_6$ only due to the vibration thereof by employing results of equation (7) with equation (4). It is noted that equation (7) may be incorporated in equation (4) resulting in a single equation to be solved without estimating) $\vec{F}(t)$ as follows:

$$\vec{s}(t) = \vec{S}(t) - M[M^T M]^{-1} M^T \vec{S}(t) \quad (8)$$

It is further noted that, if the motion compensation matrix and the relative motion vector are unknown, motion compensator 114 may estimate both by employing singular value decomposition (SVD) on $\vec{S}(t)$. It is also noted that the number of regional speckle patterns employed for estimating the in-image displacement due common motion relates to the number of motion parameters (i.e., X, Y, Z, Pitch, Yaw, Roll) to be estimated. Each regional speckle pattern may be employed for estimating two motion parameters. For example, for determining the in-image displacement due to common motion in the X, Y and Z axes and about the Pitch, Yaw and Roll axes (i.e., six motion parameters), at least three regional speckle patterns should be employed.

System 100 may be employed to detect various physiological conditions characterized by the respective audio characteristics thereof. For example, system may be employed to detect heart arrhythmia, asthma, apnea, pneumonia and the like. To that end, memory 108 stores a plurality of audio characteristics corresponding to various known physiological conditions (i.e., may include the audio characteristics corresponding to normal physiological conditions). Processor 106 compares the determined audio characteristics corresponding to each selected one of body surface locations $118_1$-$118_6$ of interest with the stored audio characteristics (i.e., associated with substantially the same body surface locations) of known physiological conditions, to determine a correspondence there between. Alternatively or additionally, processor 106 compares the determined audio characteristics corresponding to each body surface locations of interest with the audio characteristics corresponding to other ones of selected body surface locations of interest.

Following is an example of attempting to detect physiological conditions according to determined and stored sound characteristics. Initially, processor 106 filters signals of interest (e.g., sounds relating to the heart, sound relating to breathing and the like) from the detected sound signals associated with selected ones of body surface locations $118_1$-$118_6$. Such filtering may be done in the frequency domain or in the time domain. For example, heart sounds exhibit a higher frequency than breathing sounds, breathing sounds may be detected after the occurrence of a PQR cycle. For each signal on interest, processor 106 determines a respective spectrogram. Processor 106 then compares the spectrogram of each signal of interest with a reference spectrogram (e.g., associated with known physiological condition) associated with substantially the same body surface location. For example, processor 106 compares the intensities of the spectrograms corresponding to the selected ones of body surface locations relative to the intensities of the reference spectrograms (i.e., also corresponding to the same selected body surface locations). As a further example, processor 106 may cross-correlate the determined spectrograms with the reference spectrograms or cross-correlate portions of the determined spectrograms with portions of the reference spectrograms. Alternatively or additionally, processor 106 compares the spectrogram of each signal of interest with the spectrogram corresponding to other ones of selected body surface locations (e.g., comparing the spectrogram corresponding to the left lower lung with the spectrogram corresponding to the right lower lung). As described above, processor 106 may compare the intensities of these spectrograms or cross-correlate these spectrograms (i.e. or portions thereof). It is noted that spectrograms are brought herein as an example only, the above described may be employed with any one determined audio characteristics. For example, processor 106 may compare a determined sound signal with a stored sound signal by cross-correlating the two signals. Processor 106 may determine a correlation matrix between the determined sound signals which is related to the variance between the detected sound signals.

As mentioned above, the audio characteristics corresponding to body surface locations $118_1$-$118_6$ may be produced from within the body (e.g., by an organ such as the heart, the lungs, the intestines or by an embryo). When the audio characteristics include a signal representing the sound produced from within the body, processor 106 may provide that sound signal to audio reproduction sub-system 112. Audio reproduction sub-system 112 (e.g., speakers or earphones) re-produces the sound from within the body for the user to hear. Audio reproduction sub-system 112 may be a 'three-dimensional (3D) audio' reproduction sub-system as further explained below. Processor 106 may provide the determined audio characteristics to display 110 which presents graphical representations of the audio characteristics to the user. For example, display 110 may present a graph of the sound signal or a graph of the spectrum of the sound signal or both. Alternatively or additionally, display 110 displays an image of the speckle pattern or the region of interest of the body surface or of the inner body. Display 110 may be a part of a user interface, as further explained below in conjunction with FIGS. 4A and 4B.

As mentioned above, in the example set forth in FIG. 1, each regional speckle patterns $126_1$-$126_6$ is also associated with a different respective speckle pattern. However, that is not generally the case, two or more regional speckle patterns may be associated with a different portion of the same speckle pattern produced by a single beam. Nevertheless, each regional speckle pattern is associated with a respective different body surface location. Also, six body surface locations (i.e., body surface locations $118_1$-$118_6$) are brought herein as an example only. Less or more body surface location may be employed (e.g., according to user selection) as further elaborated below in conjunction with FIGS. 4A and 4B.

Figure 3:
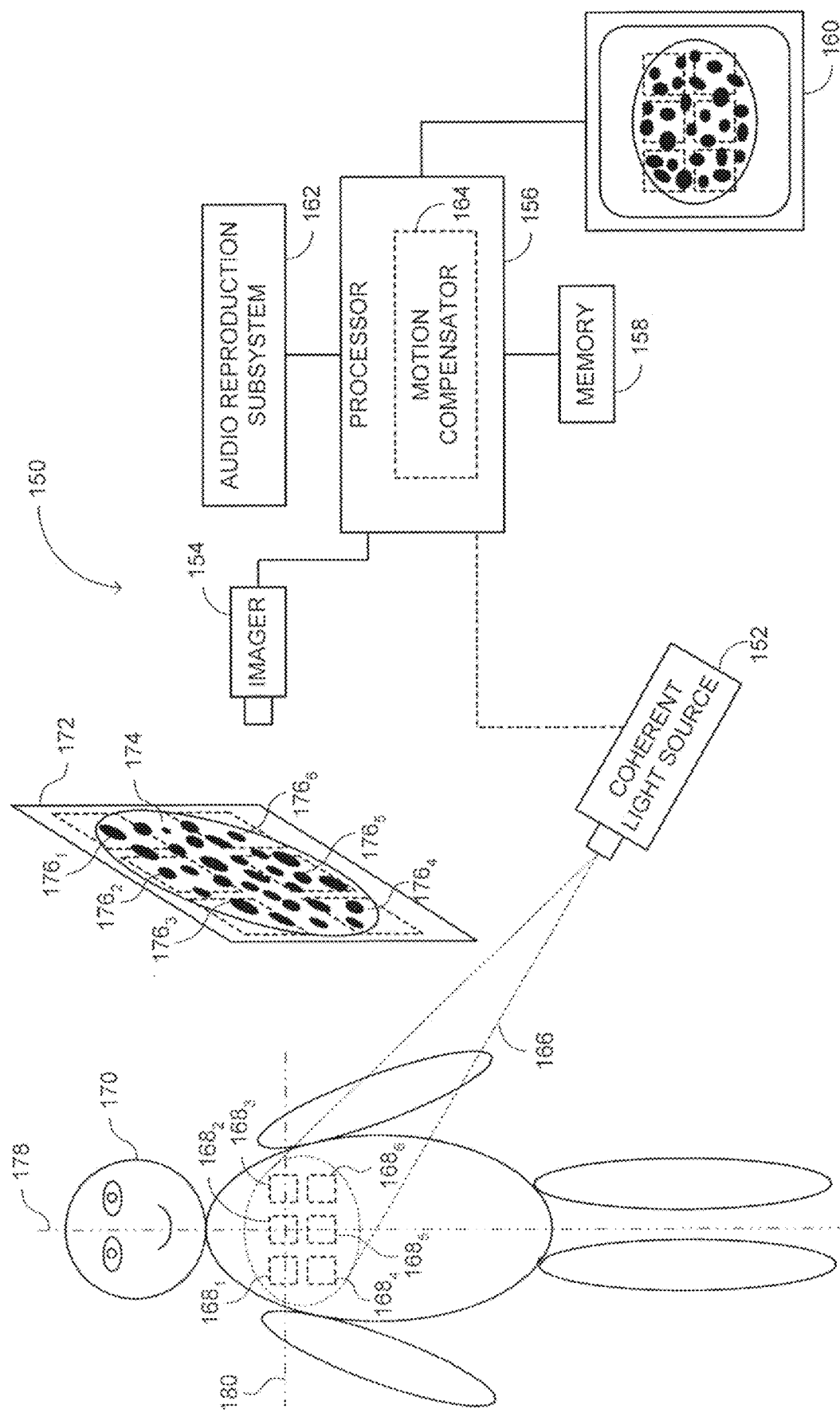
FIG. 3 is a schematic illustration of a system for simultaneously detecting audio characteristics within a body, over multiple body surface locations, constructed and operative in accordance with another embodiment of the disclosed technique.

System 100 described hereinabove in conjunction with FIG. 2 employs a plurality of coherent light beams each illuminating body surface locations. However, a single coherent light beam, which illuminates the entire body region of interest (e.g., the thorax, the abdomen) may be employed. This body region of interest includes all the plurality of body surface locations of interest. Reference is now made to FIG. 3, which is a schematic illustration of a system, generally referenced 150, for simultaneously detecting audio characteristics within a body, over multiple body surface locations, constructed and operative in accordance with another embodiment of the disclosed technique. System 150 includes a coherent light source 152, an imager 154, a processor 156, a memory 158, a display 160 and an audio reproduction sub-system 162. Processor 156 includes a motion compensator 164. Processor 156 is coupled with imager 154, memory 158, display 160 and with audio reproduction sub-system 162. Processor 156 is optionally coupled with coherent light source 152 (i.e., as indicated by the hatched line in FIG. 3).

Similarly to coherent light source 102 (FIG. 2), coherent light source 152 emits monochromatic light. Coherent light source 152 is, for example, a laser light source. Similarly to imager 104 (FIG. 2), imager 154 includes an imager sensor array (not shown) such as a Charged Coupled Device (CCD) sensor array or Complementary Metal Oxide Semiconductor (CMOS) sensor array sensitive at the frequency of the light emitted by coherent light source 152.

Coherent light source 152 emits a light beam 166 toward plurality of body surface locations $168_1$, $168_2$, $168_3$, $168_4$, $168_5$ and $168_6$ of patient 170. Light beam 166 impinges on a body region of interest of patient 170 and diffusively reflects therefrom, which results in a speckle pattern. As mentioned above, the speckle pattern varies with the vibrations of the respective one of body surface locations $168_1$-$168_6$, which may be partially induced by sound produced from within the body. It is also noted that six body surface locations (i.e., body surface locations $168_1$-$168_6$) are brought herein as an example only. Less or more body surface locations may be employed.

Imager 154 acquires a plurality of defocused images, such as image 172, of a reflection of light beam 166 from body surface locations $168_1$-$168_6$. Each image includes a speckle pattern such as speckle pattern 174 corresponding to light beam 166 reflected form body surface locations $168_1$-$168_6$. Imager 154 further associates each image with a respective time-tag, and provides the images acquired thereby to processor 156.

Processor 156 determines in-image displacement of each of a plurality of regional speckle patterns $176_1$, $176_2$, $176_3$, $176_4$, $176_5$ and $176_6$ according to the acquired images. Each one of the regional speckle patterns $176_1$-$176_6$ is associated with a respective different one of the body surface locations $168_1$-$168_6$ and thus, with a different portion of speckle pattern 174. Processor 156 determines the vibrations of each one of body surface locations $168_1$-$168_6$. These vibrations may be caused by sound produced from within the body at the body surface locations $168_1$-$168_6$. Thus, processor 156 determines the audio characteristics at body surface location $168_1$-$168_6$ according to in-image displacement of the respective regional speckle patterns $176_1$-$176_6$ similarly to as described above in conjunction with FIG. 1 and Equation 1. Alternatively, Processor 156 determines the vibrations of each one of body surface locations $168_1$-$168_6$, and thus of the audio characteristics thereof, according to variation of selected seed points also as described above. As mentioned above, the audio characteristics corresponding to body surface locations $168_1$-$168_6$ may be produced from within the body. Furthermore, motion compensator 164 compensates for the relative motion between of patient 170 and imager 154 similar to as described above in conjunction with FIG. 1 and equations 2-8. Also similar to as described above in conjunction with FIG. 1, at least some of body surface locations $168_1$-$168_6$ may partially overlap with each other thereby increasing the spatial resolution of the system.

Further similar to system 100 (FIG. 2), system 150 may be employed to detect various physiological conditions. To that end, memory 158 stores a plurality of audio characteristics corresponding to various known physiological conditions. Processor 156 then compares the determined audio characteristics corresponding to each selected one of body surface locations $168_1$-$168_6$ with reference audio characteristics (e.g., associated with known physiological condition) associated with substantially the same body surface location. Alternatively or additionally, processor 156 compares the determined audio characteristics corresponding to each body surface locations of interest with the audio characteristics corresponding to other ones of selected body surface locations of interest.

Similar to as described above in conjunction with FIG. 1, when the audio characteristics include a signal representing the sound produced from within the body, processor 156 may provide that sound signal to audio reproduction sub-system 162, which re-produces the sound from within the body for the user to hear. Audio reproduction sub-system 162 may also be a 3D audio reproduction sub-system. Also similar to as described above in conjunction with FIG. 1, Processor 156 may provide the determined audio characteristics to display 160 which presents graphical representations of the audio characteristics to the user. Alternatively or additionally, display 160 displays an image of the speckle pattern or the region of interest of the body surface or of the inner body. Display 156 may also be a part of a user interface.

In a system according to the disclosed technique (e.g., system 100 of FIG. 2 or system 150 of FIG. 3), a user may select locations of interest with the aid of a user interface (UI). For example, when a user wants to listen to the sounds produced by an embryo, the user selects body surface locations located on the abdomen. As a further example, when a user may want to listen to the sounds produced by the left lung, the user selects body surface locations located on left thorax. Alternatively, the display displays a model of the inner body region of interest or of the embryo and the user selects the body surface locations with the aid of this model.

Figure 4A:
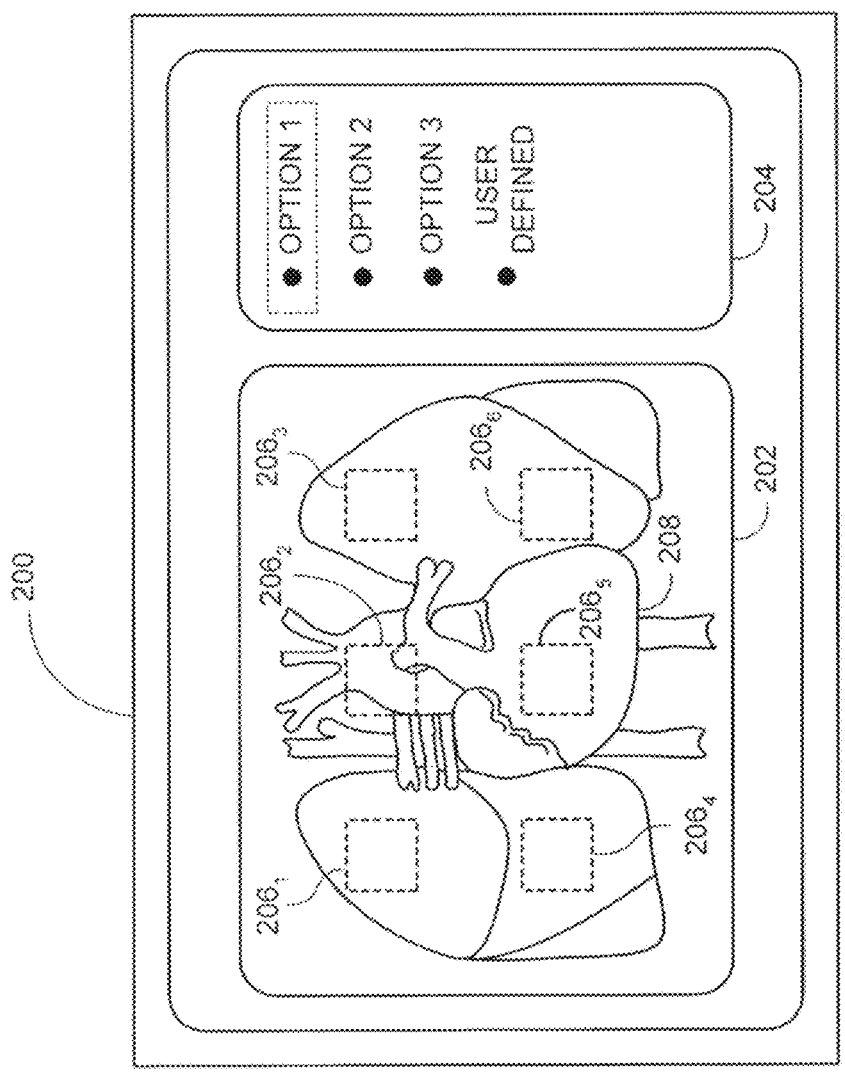
FIGS. 4A and 4B are schematic illustration of an exemplary user interface constructed and operative in accordance with a further embodiment of the disclosed technique.
Figure 4A:
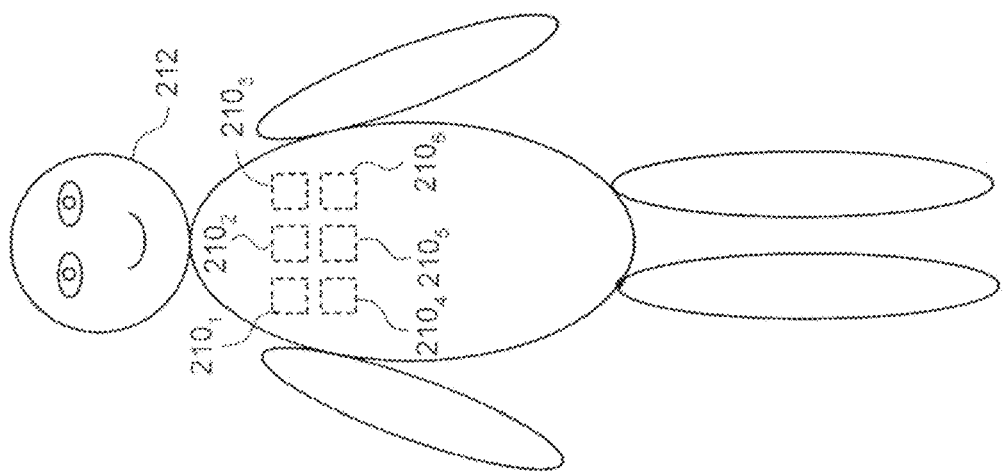
Figure 4B:
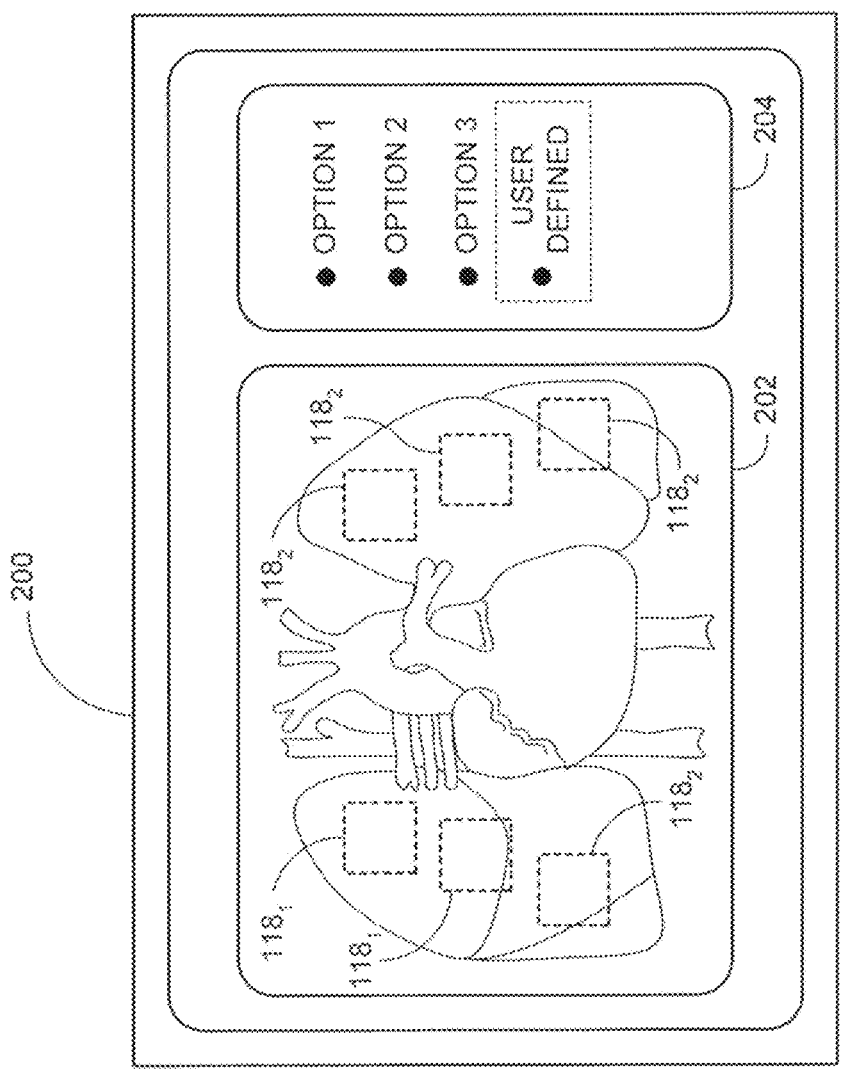
Figure 4B:
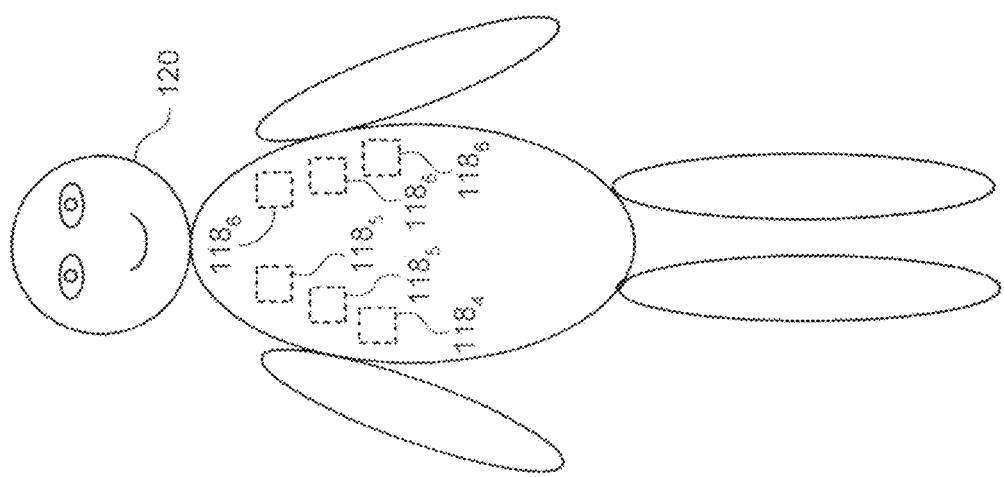

Reference is now made to FIGS. 4A and 4B which are schematic illustration of an exemplary user interface, generally referenced 200, constructed and operative in accordance with a further embodiment of the disclosed technique. User interface 200 may be employed with either one of system 100 or system 150 described hereinabove in conjunction with FIG. 2 and FIG. 3 respectively. As such user interface is coupled with the respective one of processor 110 (FIG. 2) or processor 160 (FIG. 3). User interface 200 includes a display 202 and a user selection 204. In FIGS. 4A and 4B, display 202 displays a location representations $206_1$, $206_2$, $206_3$, $206_4$, $206_5$ and $206_6$, superimposed on a model of an organ of interest 208 (e.g., the heart and the lungs in FIGS. 4A and 4B). Each one of location representations $206_1$-$206_6$ corresponds to a respective body surface location $210_1$, $210_2$, $210_3$, $210_4$, $210_5$ and $210_6$ on the body of patient 210. A user selects the body surface locations $210_1$-$210_6$ of interest according to the location of location representations $206_1$-$206_6$ on display 202. The user may select the body surface locations $208_1$-$208_6$ of interest by employing user selection 204. In the example set forth in FIGS. 4A and 4B, user selection 204 includes predefined options and a user defined option. Each of the predefined options includes a different selection of body surface locations $210_1$-$210_6$ suitable for a known situation. For example, option one depicted in FIG. 4A includes body surface locations suitable for determining the audio characteristics corresponding to the heart and lungs of a male adult. Similarly, option two includes body surface locations suitable for determining the audio characteristics corresponding to the heart and lungs of a female adult. Option three includes body surface locations suitable for determining the audio characteristics corresponding to the heart and lungs of a child (i.e., the location representations $206_1$-$206_6$ and the corresponding body surface locations $210_1$-$210_6$ will be more densely distributed than body surface locations $210_1$-$210_6$ of an adult).

With reference to FIG. 4B, when employing the user defined option in user interface 200, the user may select the body surface locations $210_1$-$210_6$ by moving location representations $206_1$-$206_6$ (e.g., with the aid of a cursor) on display 202 to the desired location. In the example set forth in FIG. 4B, the user selects to determine the audio characteristics corresponding to the lungs only. When user interface 200 is employed in conjunction with system 100 (FIG. 2), and the user selects body surface locations $210_1$-$210_6$ by moving location representations $206_1$-$206_6$, coherent light source 102 shall direct the light beams emitted thereby toward selects body surface locations $210_1$-$210_6$ according to the location of location representations $206_1$-$206_6$ on display 202. Furthermore location representations $206_1$-$206_6$ shall indicated the location of the regional speckle patterns $126_1$-$126_6$ in the images acquired by imager 104. When user interface 200 is employed in conjunction with system 150 (FIG. 3), and the user selects body surface locations $210_1$-$210_6$ by moving location representations $206_1$-$206_6$, coherent light source 152 shall directs the light beam emitted thereby toward body surface region of interest according to the location of location representations $206_1$-$206_6$ on display 202. Furthermore location representations $206_1$-$206_6$ shall indicate the location of the regional speckle patterns $176_1$-$176_6$ in the images acquired by imager 154. For a user to be able to select body surface locations $210_1$-$210_6$ with the aid of user interface 200 and a model an organ of interest 208, the coordinate system associated with the model (herein 'the model coordinate system') and the coordinate system associated with the image acquired by the imager should be registered with each other (e.g., with the aid of fiducials) so the selection of location representations $206_1$-$206_6$ shall corresponds to the body surface locations $210_1$-$210_6$. Furthermore, the time delay between signals, originating from the same source and measured at different body locations may be employed to determine the exact position of the sound source. For example, each time delay fits to a hyperbola in the model coordinate system supposing a uniform propagation velocity. An intersection of at least two of such hyperbolas defines a two dimensional location of the sound source. Also comparing between signals gathered at different defined positions the various internal body sounds (e.g., the sound of breathing) may be characterized, for example, in terms of the above mentioned audio characteristics.

As mentioned above, audio reproduction sub-system 112 (FIG. 2) and audio reproduction sub-system 162 (FIG. 3) may be a 3D audio reproduction sub-system. Such a 3D audio reproduction sub-system reproduces the sound detected from within the body, which the user hears as originating from the source of the sound (e.g., from the heart of the patient). To that end, for example, the processor employs a Head Related Transfer Function (HRTF) to produce a binaural sound to be reproduced on headphones. In general, for a 3D audio reproduction system to produce the sound, which the user hears as originating from the source of the sound, the spatial relationship between the source and the user should be known (i.e., either fixed or tracked). For example, the user may position herself in front of the patient at a fixed relative position during examination. Alternatively, the spatial relationship between the user and the source may be tracked by a tracking system (e.g., an optical tracking system, an electromagnetic tracking system or an ultrasound tracking system). The output of such a tracking system is used as the input for the HRTF.

Figure 5:
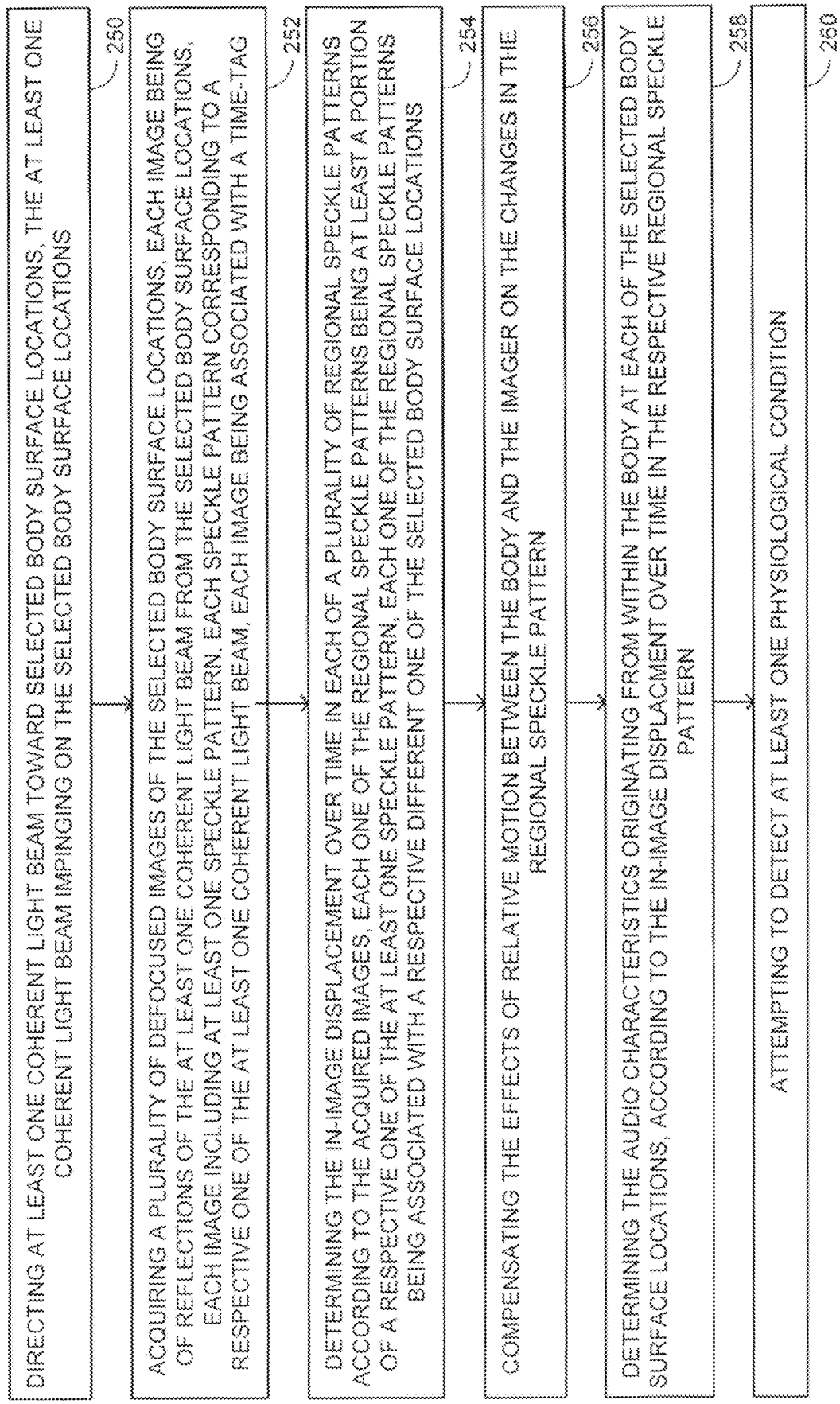
FIG. 5 is a schematic illustration of a method for simultaneously detecting audio characteristics within a body, over multiple body surface locations, operative in accordance with another embodiment of the disclosed technique.

Reference is now made to FIG. 5, which is a schematic illustration of a method for simultaneously detecting audio characteristics within a body, over multiple body surface locations, operative in accordance with another embodiment of the disclosed technique. In procedure 250, at least one coherent light beam is directed toward body surface locations. The at least one coherent light beam impinges on the body surface locations. With reference to FIG. 2, coherent light source 102 directs a plurality of coherent light beams toward body surface locations $118_1$-$118_6$. With reference to FIG. 3, coherent light source 152 directs coherent light beams 266 toward body surface locations $168_1$-$168_6$.

In procedure 252, a plurality of defocused images of the body surface locations are acquired. Each image is reflections of the at least one coherent light beam from the body surface locations. Each one of the images includes at least one speckle pattern, each speckle pattern corresponding to a respective one of the at least one coherent light beam. Each one of the images being further associated with a respective time-tag. With reference to FIG. 2, imager 104 acquires a plurality of defocused images of body surface locations $118_1$-$118_6$, each including at least one speckle pattern corresponding to a respective coherent light beam. With reference to FIG. 3, imager 154 acquires a plurality of defocused images of body surface locations $168_1$-$168_6$, each including at least one speckle pattern corresponding to a respective coherent light beam.

In procedure 254, the in-image displacement over time of each of a plurality of regional speckle patterns are determined according to the acquired images. Each regional speckle pattern is at least a portion of a respective one of the at least one speckle pattern. Each regional speckle pattern is associated with a respective different one of the body surface locations. With reference to FIG. 2 processor 106 determines the in-image displacements over time of each of a plurality of regional speckle patterns according to the acquired images. With reference to FIG. 3 processor 156 determines the in-image displacement over time of each of a plurality of regional speckle patterns according to the acquired images.

In procedure 256, the effects of relative motion between the body and the imager on the in-image displacements of the regional speckle pattern are compensated. As mentioned above, the relative motion between the body and the imager may result in an additional shift in the regional speckle patterns other than the shift caused by the vibration of the body surface locations. The effect of the relative motion between the body and the imager on the in-image displacements of the regional speckle pattern is compensated as described above in conjunction with equations 2-7. With reference to FIG. 2, motion compensator 114, compensate the effect of the relative motion between the body of patient 120 and the imager 102 on the in-image displacement of the regional speckle pattern $126_1$-$126_6$. With reference to FIG. 3, motion compensator 164, compensates the effects of relative motion between the body of patient 170 and the imager 152 on the in-image displacements of the regional speckle pattern $176_1$-$176_6$. It is noted that when no relative motion exists between the body (e.g., when both the body and the imager cannot move) there is no need to compensate the effects such relative motion.

In procedure 258, the audio characteristics originating from within the body, at each of the body surface locations, are determined according to the in-image displacements over time of the respective regional speckle pattern. As mentioned above, sound originating from within the body may result in vibrations of the body surface. With reference to FIG. 2, processor 106 determines the audio characteristics originating from within the body at each of the body surface locations according to the in-image displacements over time of the respective regional speckle pattern. With reference to FIG. 3, processor 156 determines the audio characteristics originating from within the body at each of the body surface locations according to the in-image displacements over time of the respective regional speckle pattern.

In procedure 260, the detection of at least one physiological condition is attempted. A physiological condition may be detected by comparing the determined audio characteristics corresponding to each selected one of body surface locations with reference audio characteristics corresponding to substantially the same body surface location. Alternatively or additionally, a physiological condition may be detected by comparing the determined audio characteristics corresponding to each body surface locations of interest with the audio characteristics corresponding to other ones of selected body surface locations of interest. With reference to FIG. 2, memory 108 stores a plurality of audio characteristics corresponding to various known physiological conditions. Processor 106 compares the determined audio characteristics corresponding to each selected one of body surface locations $118_1$-$118_6$ of interest with the stored audio characteristics corresponding to known physiological conditions, to determine a correspondence there between. Alternatively or additionally, processor 106 compares the determined audio characteristics corresponding to each body surface locations of interest with the audio characteristics corresponding to other ones of selected body surface locations of interest. With reference to FIG. 3, memory 158 stores a plurality of audio characteristics corresponding to various known physiological conditions. Processor 106 then compares the determined audio characteristics corresponding to each selected one of body surface locations $168_1$-$168_6$ with reference audio characteristics corresponding to substantially the same body surface location. Alternatively or additionally, processor 156 compares the determined audio characteristics corresponding to each body surface locations of interest with the audio characteristics corresponding to other ones of selected body surface locations of interest.

Figure 6A:
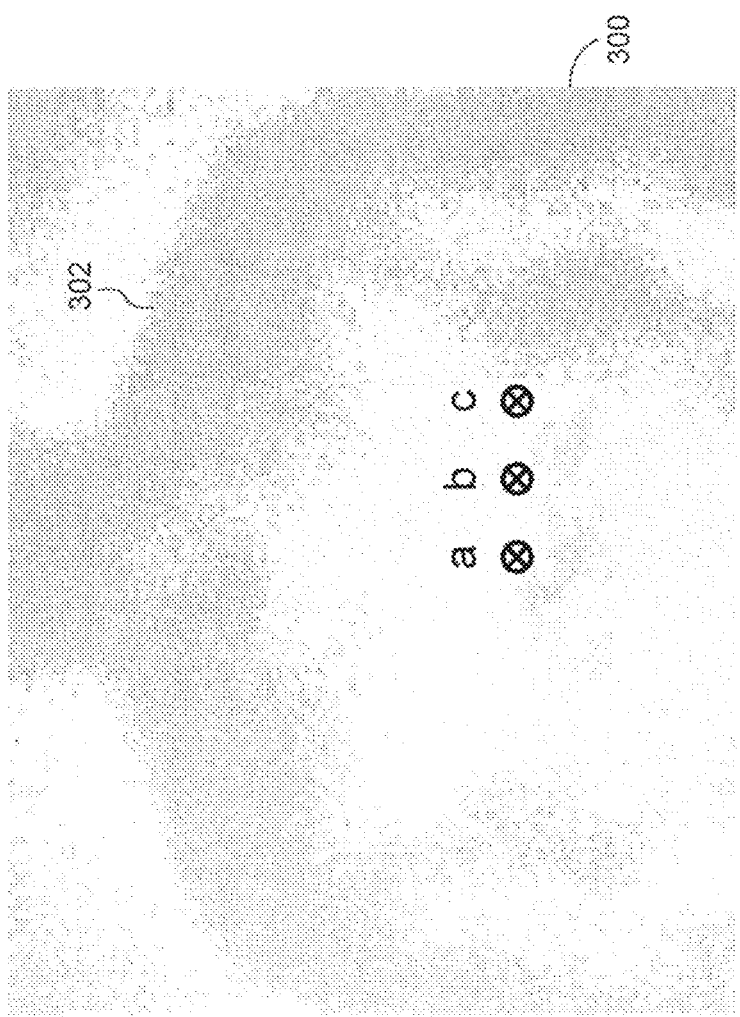

Reference is now made to FIGS. 6A-6D, which are schematic illustrations of an example for simultaneously detecting audio characteristics within a body, over multiple body surface locations, in accordance with another embodiment of the disclosed. FIG. 6A depicts an acquired defocused image 300 of a thorax of a patient 302 illuminated with a single beam of coherent light. Superimposed on image 300 are markings, 'a', 'b' and 'c' of body surface locations from which audio characteristics are detected. Each of body surface locations 'a', 'b' and 'c' is associated with a respective regional speckle pattern (e.g., regional speckle patterns $176_1$-$176_6$ in FIG. 3). With reference to FIGS. 6B-6D, FIG. 6B depicts the audio characteristic 304 detected from body surface location 'a', FIG. 6C depicts the audio characteristic 306 detected from body surface location 'b', FIG. 6D depicts the audio characteristic 308 detected from body surface location 'c'. In FIGS. 6B-6D, detected audio characteristic 304, 306 and 308 are sound signals from the heart of patient 302 where the horizontal axis is related to time and the vertical axis is related to amplitude.

It will be appreciated by persons skilled in the art that the disclosed technique is not limited to what has been particularly shown and described hereinabove. Rather the scope of the disclosed technique is defined only by the claims, which follow.

The invention claimed is:

1. A system for simultaneously detecting audio characteristics within a user's body, over multiple body surface locations, the system comprising:
a coherent light source, directing at least one coherent light beam toward and reflected from said body surface locations;
an imager, configured to acquire a plurality of defocused images of said reflections, each image including at least one speckle pattern, each speckle pattern corresponds to said at least one coherent light beam, each image being associated with a time-tag;
a processor, coupled with said imager, said processor determining in-image displacements over time of each of a plurality of regional speckle patterns in said acquired images, each of said regional speckle patterns being at least a portion of said at least one speckle pattern, each one of said regional speckle patterns corresponding to a different one of said body surface locations, said processor determining said audio characteristics according to said in-image displacements over time of said regional speckle patterns.

2. The system according to claim 1, further including a memory and audio characteristics corresponding to known physiological condition, said memory storing the audio characteristics corresponding to the known physiological condition.

3. The system according to claim 2, wherein said processor determines whether said determined audio characteristics corresponds to at least one known physiological condition by comparing said determined audio characteristics corresponding to each selected one of body surface locations of interest with said stored audio characteristics corresponding to the known physiological condition.

4. The system according to claim 2, wherein said processor determines whether said determined audio characteristics corresponds to at least one known physiological condition by comparing the audio characteristics corresponding to each body surface locations of interest with the audio characteristics corresponding to other ones of selected body surface locations of interest.

5. The system according to claim 1, further includes an audio reproduction subsystem configured to reproduce sounds corresponding to said audio characteristics.

6. The system according to claim 5, wherein said audio reproduction subsystem is a three-dimension audio reproduction system configured to reproduce sound corresponding to said audio characteristics, which the user hears as originating from a source of the reproduced sound.

7. The system according to claim 6, wherein said processor employs a Head Related Transfer Function to produce a binaural sound to be reproduced on headphones.

8. The system according to claim 4, wherein said body surface locations correspond to regions of interest and where said region of interest is one of a thorax and an abdomen.

9. The system according to claim 1, wherein said audio characteristics are at least one of
an audio signal;
an audio spectrogram;
spectrum;
sound pressure level;
sound power;
time delay between signals measured on different body surface locations; and energy.

10. The system according to claim 1, wherein said processor further includes a motion compensator, said motion compensator is configured to compensate for effects on the in-image displacement of each respective regional speckle pattern corresponding to a relative motion between said imager and each of said body surface locations.

11. The system according to claim 10, wherein said motion compensator compensates said effects according to the following:

$$\vec{s}(t)=\vec{S}(t)-M[M^TM]^{-1}M^T\vec{S}(t)$$

wherein s(t) relates to the in-image displacement of said regional speckle pattern corresponding to said body surface locations, wherein said body surface locations are vibrating, said in-image displacement is only due to the vibrations of said body surface locations, S(t) relates to the in-image displacement of the regional speckle pattern corresponding to said body surface locations due to both the relative motion between said imager and each of said body surface locations and the vibrations of said body surface locations and M is a motion compensation matrix.

12. The system according to claim 1, further including a display for displaying at least one of:
said speckle patterns; and
a visual representation of said audio characteristics.

13. The system according to claim, 12 further including a user interface, said user interface including said display and a user selector, said selector allows selection of said body surface locations according to one of predefined options and user defined locations.

14. The system according to claim 13, wherein, said body surface locations correspond to inner body locations and said body surface location are selected according to the inner body location for which said audio characteristics are to be determined.

15. A method for simultaneously detecting audio characteristics within a user's body, over multiple body surface locations, the method comprising the procedures of:
directing at least one coherent light beam toward said body surface locations, said at least one coherent light beam impinging on said body surface locations;
acquiring a plurality of defocused images reflected said coherent light from said body surface, wherein each image includes at least one speckle pattern corresponding to said at least one coherent light beam, and each image being associated with a time-tag;
determining an in-image displacement over time in each of a plurality of regional speckle patterns, wherein each one of said regional speckle patterns being at least a portion of a respective one of said at least one speckle pattern and each one of said regional speckle patterns being associated with a respective one of said body surface locations; and determining the audio characteristics originating from within the body at each of said body surface locations according to the in-image displacement over time in respective regional speckle patterns.

16. The method according to claim 15, further includes the step of attempting to detect at least one physiological condition.

17. The method according to claim 16, wherein said determined audio characteristics corresponding to each selected one of body surface are compared with reference audio characteristics corresponding to substantially the same body surface location thereby attempting to detect at least one physiological condition.

18. The method according to claim 16, wherein said determined audio characteristics corresponding to each body surface locations of interest are compared with the audio characteristics corresponding to other audio characteristics of other selected body surface locations of interest.

19. The method according to claim 15, further including the step of compensating effects of relative motion between the body and imager on the regional speckle pattern.

20. The method according to claim 19, wherein said effects of relative motion between the body and the imager are compensated according to the following:

$$\vec{s}(t)=\vec{S}(t)-M[M^TM]^{-1}M^T\vec{S}(t)$$

wherein s(t) relates to the in-image displacement of said regional speckle pattern corresponding to said body surface locations where said body surface locations are vibrating, only due to the vibration of said body surface locations, S(t) relates to the in-image displacement of the regional speckle pattern corresponding to said body surface locations due to both the relative motion between said imager and each of said body surface locations and the vibrations of said body surface locations and M is a motion compensation matrix.

21. The method according to claim 15, wherein said body surface locations correspond to regions of interest and where said regions of interest are one of a thorax and an abdomen.

22. The method according to claim 15, wherein said audio characteristics are at least one of:
an audio signal;
an audio spectrogram
spectrum;
sound pressure level;
sound power;
time delay between signals measured on different body surface locations; and
energy.

23. The method according to claim 15, wherein said body surface locations are selected according to one of predefined options and user defined locations.

24. The system according to claim 15, wherein, said body surface locations correspond to inner body locations and are selected according to the inner body location for which said audio characteristics are to be determined.

* * * * *